US006558330B1

(12) United States Patent
Ayter et al.

(10) Patent No.: US 6,558,330 B1
(45) Date of Patent: May 6, 2003

(54) STACKED AND FILLED CAPACITIVE MICROELECTROMECHANICAL ULTRASONIC TRANSDUCER FOR MEDICAL DIAGNOSTIC ULTRASOUND SYSTEMS

(75) Inventors: Sevig Ayter, Cupertino, CA (US); John W. Sliwa, Jr., Los Altos, CA (US)

(73) Assignee: Acuson Corporation, Mountain View, CA (US)

( * ) Notice: Subject to any disclaimer, the term of this patent is extended or adjusted under 35 U.S.C. 154(b) by 18 days.

(21) Appl. No.: 09/731,597

(22) Filed: Dec. 6, 2000

(51) Int. Cl.[7] .................................................. A61B 8/00
(52) U.S. Cl. ...................................................... 600/459
(58) Field of Search ................................ 600/459, 443, 600/437, 444; 690/460; 310/334; 367/170, 140

(56) References Cited

U.S. PATENT DOCUMENTS

| | | | | |
|---|---|---|---|---|
| 5,548,564 A | * 8/1996 | Smith | | 367/140 |
| 5,619,476 A | 4/1997 | Haller et al. | | |
| 5,744,898 A | * 4/1998 | Smith et al. | | 310/334 |
| 5,870,351 A | 2/1999 | Ladabaum et al. | | |
| 5,894,452 A | 4/1999 | Ladabaum et al. | | |
| 5,957,851 A | 9/1999 | Hossack | | |
| 5,982,709 A | * 11/1999 | Ladabaum et al. | | 367/170 |
| 6,004,832 A | 12/1999 | Haller et al. | | |
| 6,087,762 A | * 7/2000 | Corbett | | 310/334 |
| 6,121,718 A | 9/2000 | Mohr, III | | |
| 6,328,697 B1 | * 12/2001 | Fraser | | 600/459 |

OTHER PUBLICATIONS

H.T. Soh et al., *Silicon micromachined Ultrasonic Immersion Transducer*, Appl. Phys. Lett. 69 (24), Dec. 9, 1996; pp. 3674–3676.

Peter–Christian Eccardt et al., *Surface micromachined ultrasound transducer in CMOS technology*; 1996 IEEE Ultrasonics Symposium; pp. 959–962.

Peter–Christian Eccardt et al., *Micromachined Transducers for Ultrasound Applications*, 1997; IEEE Ultrasonics Symposium; pp. 1609–1618.

David W. Schindel et al., *The Design and Characterization of Micromachined Air–Coupled Capacitance Transducers*; IEEE Transactions on Ultrasonics, Ferroelectrics and Frequency Control, vol. 42, No. 1, Jan. 1995; pp. 42–50.

Matthew I. Haller et al., *A Surface Micromachined Electrostatic Ultrasonic Air Transducer*, 1994; IEEE Ultrasonics Symposium; pp. 1241–1244.

Peter C. Eccardt et al., *Micromachined Ultrasound Transducers with Improved Coupling Factors from a CMOS Compatible Process*; Jul., 1999; Ultrasonics International '99 Joint with 1999 Wold Congress on Ultrasonics, Jun. 28–Jul. 1, 1999, Kopenhagen; pp. 1–6.

Kurt Niederer et al., *Micromachined Transducer Design for Minimized Generation of Surface Waves*; Oct., 1999; 1999 IEEE Ultrasonics Symposium, Oct. 18–22, 1999, Lake Tahoe; pp. 1–3.

* cited by examiner

*Primary Examiner*—Marvin M. Lateef
*Assistant Examiner*—Maulin Patel

(57) ABSTRACT

A capacitive microelectromechanical ultrasound transducer array with improved efficiency and durability is provided. Efficiency is provided by stacking CMUTs in the range dimension (i.e. away from the face of the transducer). A plurality of chambers and associated membranes are stacked along a range dimension or parallel to the direction of acoustic radiation. Because the CMUT transducer element is stacked, ultrasound is transmitted through the plurality of chambers, amplifying the response of the transducer element. Durability is increased within the transducer by filling the chamber with a nongaseous filler. A liquid, polymer, solid or plasma fills the chamber or chambers. The nongaseous filler allows movement of the membrane for transducing between acoustic and electrical energies, but prevents collapse or bottoming out of the membrane.

35 Claims, 3 Drawing Sheets

STACKED AND FILLED CAPACITIVE MICROELECTROMECHANICAL ULTRASONIC TRANSDUCER FOR MEDICAL DIAGNOSTIC ULTRASOUND SYSTEMS

BACKGROUND

This invention relates to a medical diagnostic ultrasound transducer. In particular, a capacitive microelectromechanical ultrasonic transducer and method for using the transducer are provided.

Capacitive microelectromechanical ultrasonic transducer (CMUTs) comprise transducer arrays of a single layer of chambers and associated membranes etched within a silicon wafer. CMUTs provide ultra-wideband phased arrays, and may allow integrated circuit components to be etched on the same wafer as the transducer. Each CMUT element is a hollowed chamber with a membrane subject to externally induced mechanical collapse. The chamber allows the membrane to vibrate, transferring acoustic energy away from the CMUT or converting acoustic energy into electrical signals. Each CMUT or chamber is formed using directionally selective wet or dry etching techniques.

CMUTs are inefficient as compared with conventional piezoelectric devices. For example, a typical CMUT device with a DC bias of 230 volts provides a maximum output pressure of around 33,000 Pascals per volt (P/V). In comparison, an Acuson L5 piezoelectric transducer element outputs pressure of around 46,000 P/V for transmit. Similar relative receive efficiencies are expected. More efficient devices allow lower voltage levels, reducing the complexity of transmit circuitry. In the receive mode, improved efficiency provides better signal to noise ratios, allowing improved image quality at deeper depths.

CMUT devices also have poor mechanical strength. The CMUT devices may break or become inoperable when placed in contact with tissue. The pressure applied from the tissue may collapse or adversely affect the performance of the membrane within the chamber.

BRIEF SUMMARY

The present invention is defined by the following claims, and nothing in this section should be taken as a limitation on those claims. By way of introduction, the preferred embodiments described below include a CMUT transducer array and associated method for using the CMUT transducer array with improved efficiency and durability. Efficiency is provided by stacking CMUTs in the range dimension (i.e. away from the face of the transducer). A plurality of chambers and associated membranes are stacked along a range dimension or parallel to the direction of acoustic radiation. Because the CMUT transducer element is stacked, ultrasound is transmitted through the plurality of chambers, amplifying the response of the transducer element.

Durability is increased within the transducer by filling the chamber with a nongaseous filler. A liquid, polymer, solid or gas fills the chamber or chambers. The nongaseous filler allows movement of the membrane for transducing between acoustic and electrical energies, but prevents collapse or bottoming out of the membrane.

Further aspects and advantages of the invention are discussed below in conjunction with the preferred embodiments.

DETAILED DESCRIPTION OF THE PREFERRED EMBODIMENTS

The preferred embodiments include one or both of stacking CMUTs within an element along the range dimension and filling a chamber of a CMUT with a nongaseous filler. The increased load caused by the nongaseous filler is compensated for by providing amplification through stacked CMUTs.

Figure 1:
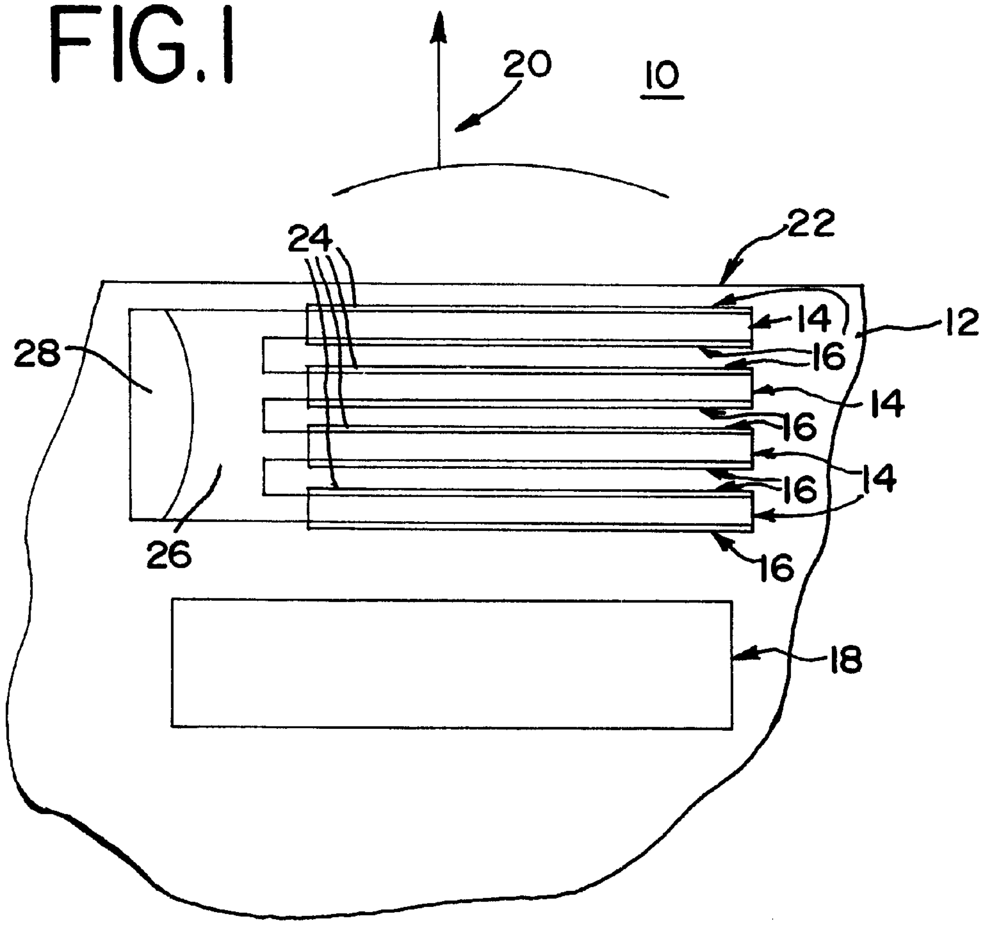
FIG. 1 is a graphical representation of a stacked CMUT.

FIG. 1 shows a single element or a portion of an element 10 in a CMUT transducer array. The element 10 includes a substrate 12, a plurality of chambers 14, a plurality of electrodes 16, and an optional attenuative backing material chamber 18. As shown, the path of radiation or propagation of ultrasonic energy or the range dimension is represented by arrow 20. Radiated acoustical energy interacts with acoustic energy from other elements to generate a scan line perpendicular or at an angle to the face of the transducer array.

The substrate 12 comprises a silicon wafer or chip. Alternatively, the substrate comprises another material, such as glass or ceramic. The substrate 12 is diced or otherwise formed such that the acoustic energy is preferably received at and transmitted from an edge 22 of the wafer or chip.

A plurality of chambers 14 are formed in the substrate 12. The chambers 14 define a plurality of membranes 24. In alternative embodiments, a single chamber 14 and associated membrane 24 are provided. Any number of stacked chambers or CMUTs may be provided. For example two or more, such as four, six or ten chambers and associated membranes are provided. The chambers are formed adjacent to each other with minimal separation and provide a plurality of layers or stacked CMUTs along a range dimension or a dimension parallel to a direction of acoustic radiation. The chambers 14 of the stack may be of the same or different sizes or configurations and be offset azimuthally and/or elevationally from adjacent layers.

The chambers 14 are formed so that the membranes 24 are around 0.1 to 1 microns thick. Greater or lesser thicknesses may be used, and membranes 24 of different layers may be different thicknesses or the same thicknesses. The chambers 14 are also 0.1 to 1 microns thick or deep along the range dimension, but may include greater or lesser depths. The depth of the chambers 14 is similar to or different than the thickness of the membranes 24, and the chambers 14 of different layers may have a different depth than other chambers 14. For example, the ratio of the thickness of the membranes 24 to the depth of the chambers 14 is selected such that electrostatic cross talk between adjacent CMUTs is significantly less than the primary driving force within each CMUT. In one embodiment, the thickness of the membrane to the chamber depth is a ratio of 1 to 5 or 1 to 10, but other thicknesses may be provided. In one embodiment, the overall depth of a ten layer stack of chambers 14 and associated membranes 24 is around 15 microns along the range dimension. The overall depth is selected to be less than the wavelength at the highest operating frequency, such as 10 megahertz. Other overall depths may be used.

Figure 2:
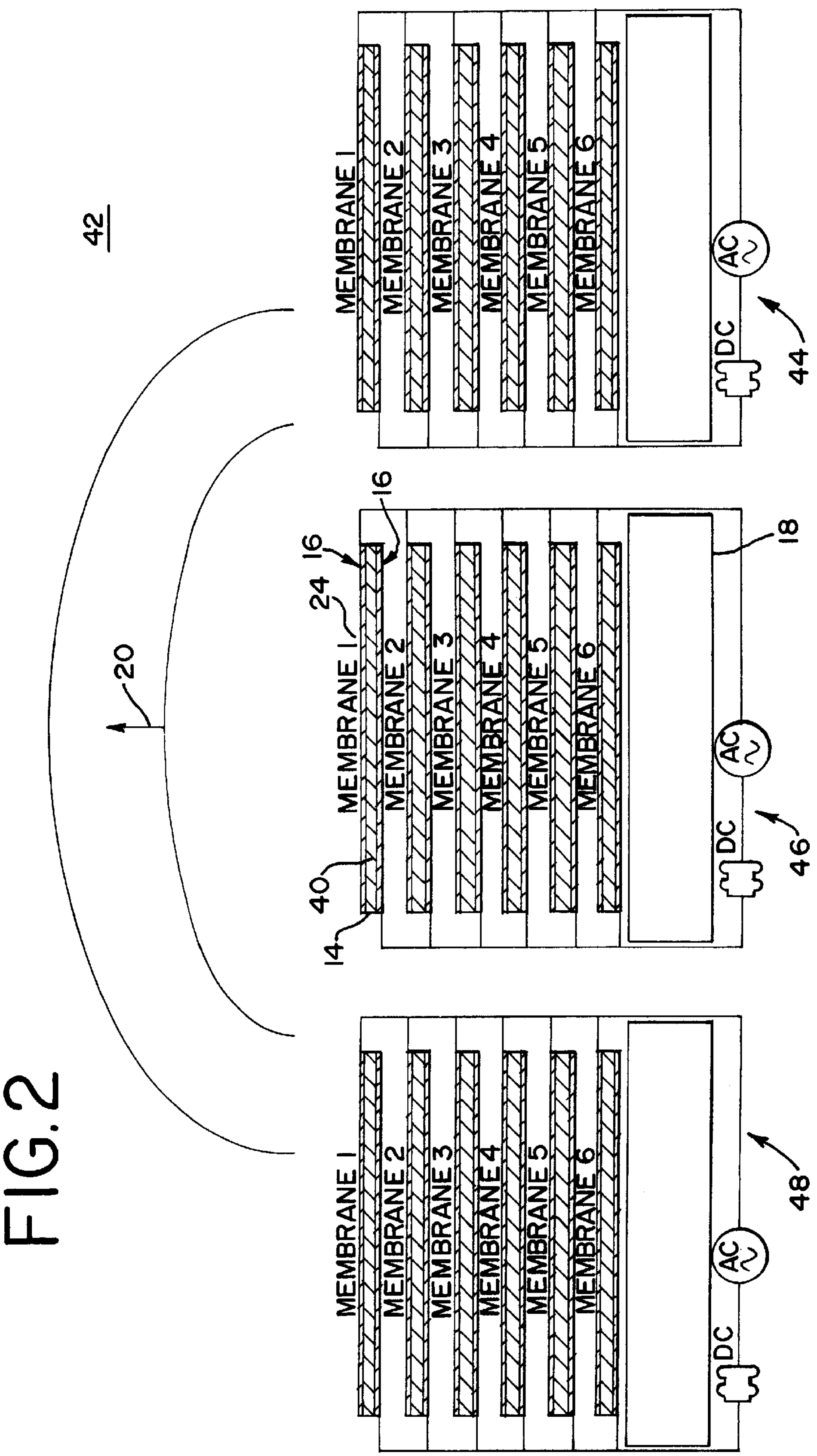
FIG. 2 is a graphical representation of an array of stacked CMUTs.
Figure 3A:
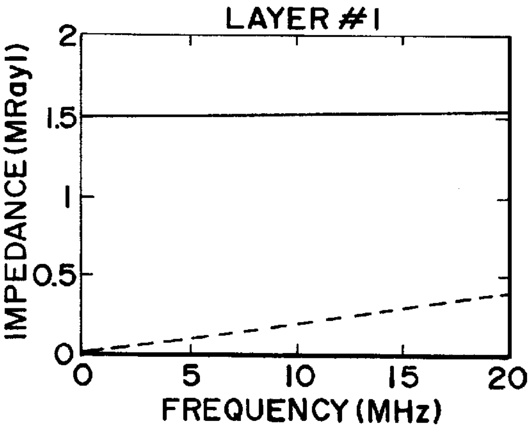
FIGS. 3A through F are graphical representations of the impedance provided as a function of different numbers of layers or chambers of a stacked CMUT.
Figure 3B:
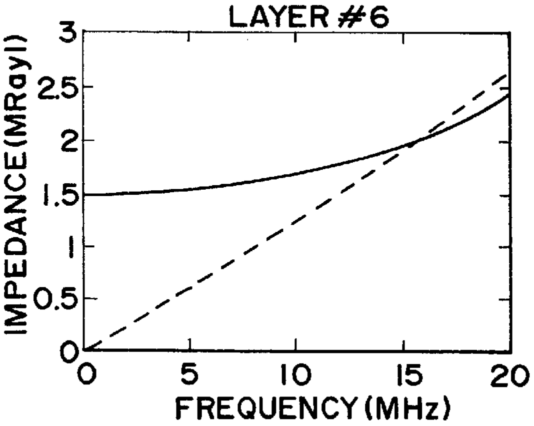
Figure 3C:
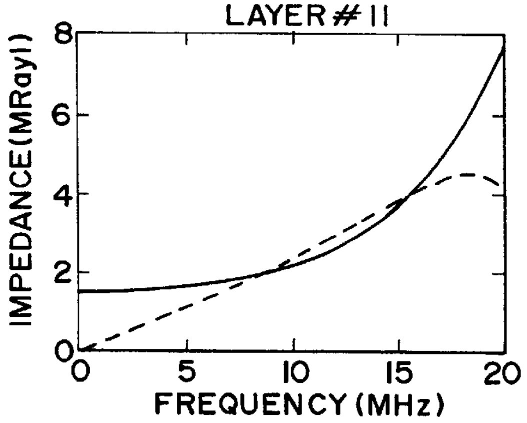
Figure 3D:
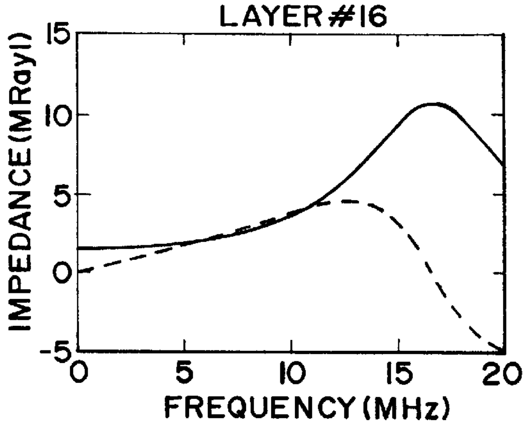
Figure 3E:
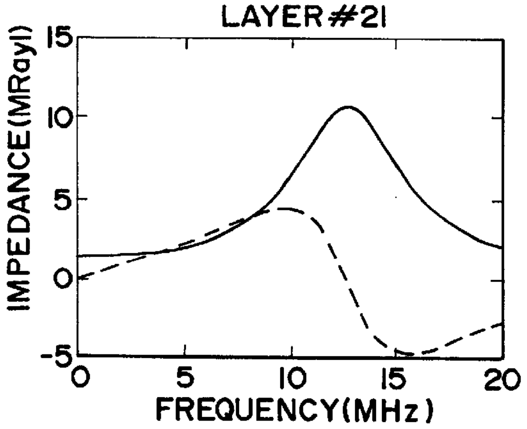
Figure 3F:
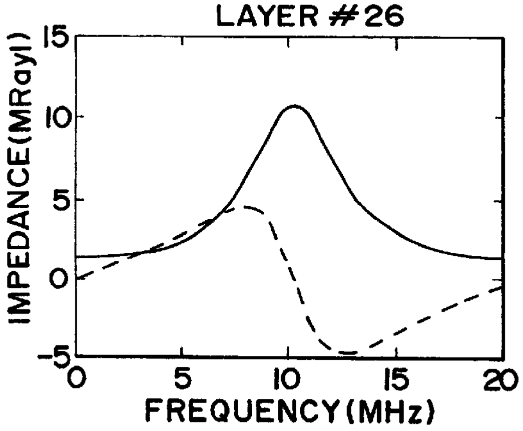

In one embodiment, such as shown in FIG. 2, each chamber 14 is isolated from the other chambers. No connection allowing liquid to travel between chambers 14 is provided. Alternatively, one or more, such as all, of the chambers 14 are interconnected. FIG. 1 shows all of the chambers 14 interconnected through a common chamber area 26.

A pair of electrodes 16 are provided within each chamber 14. In alternative embodiments, other distributions of electrodes throughout the CMUT layers, such as including only one or no electrodes in any given chamber may be used. The electrodes 16 are provided on the top and bottom surfaces along the range dimension of the chambers 14. In one embodiment, the electrodes 16 are about 500 angstroms thick.

As shown in FIG. 2, the electrodes 16 of each stack of CMUTs are commonly connected to the same DC and AC sources. For example, an upper or lower electrode 16 of each chamber 14 is connected to ground and the other of the electrode pair is connected to the signal source. In alternative embodiments, different signals are applied to different CMUTs or electrodes 16 of different chambers 14.

One or more of the chambers 14 is filled with a nongaseous filler. The nongaseous filler comprises a liquid, elastomer or polymer. For example, the nongaseous filler comprises water. In other embodiments, the nongaseous filler comprises a solid phase material. A nongaseous filler is selected with desired properties for preventing collapse or bottoming out of the membranes 24 while still most efficiently allowing transducing between electrical and acoustic energies (e.g. minimizing the dampening effect of the nongaseous filler). The nongaseous filler is selected to not support shear stresses, allowing for membrane motion within the limits of the filler inertial limitations.

Figure 4:
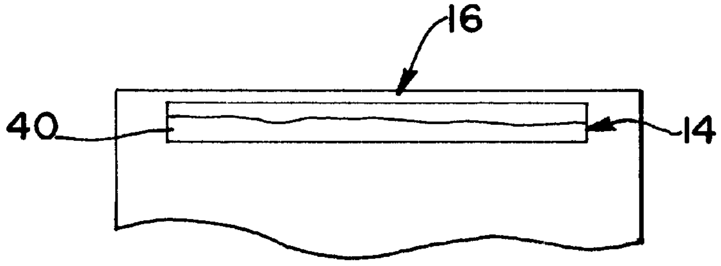
FIG. 4 is a graphical representation of a CMUT with nongaseous filler.

FIG. 4 represents a CMUT that includes the chamber 14 and the membrane 16. The chamber 14 is partially filled with nongaseous filler 40. As the membrane 16 vibrates, the membrane contacts a portion of the nongaseous filler 40. As the amplitude of the vibration 16 become greater, more of the membrane 16 contacts the nongaseous filler 40. For liquid nongaseous filler 40, the membrane 16 forces the nongaseous filler to the edges of the chamber 14. For solid phase nongaseous filler 40, the membrane 14 compresses the nongaseous filler 40. In either situation, any non linearity in the response of the membrane 16 is accounted for through signal processing or minimized by the amount and characteristics of the nongaseous filler 40. The nongaseous filler 40 within the chamber 14 allows the lateral edges or the entire membrane 16 to oscillate, reducing filler inertial loading. In alternative embodiments, the chamber 14 is entirely filled with nongaseous filler 40. The membrane 16 compresses the nongaseous filler 40 during any movement.

Referring to FIG. 1, one embodiment provides a void 28 connected with one or more of the chambers 14. For example and as shown in FIG. 1, the void 28 is within the common chamber 26 that connects with all of the chambers 14. Nongaseous filler is provided in the chambers 14 and common chamber 26. For a liquid phase nongaseous filler, the void 28 is defined by a flexible membrane or other structure preventing flow of the nongaseous filler into the void 28. For solid phase nongaseous filler, the void 28 is defined by placement of the nongaseous filler within the common chamber 26. The void 28 allows expansion of the nongaseous filler or flow of the nongaseous filler into space occupied by the void 28 in response to pressures within the chambers 14 caused by the membranes 24. In one embodiment, the void 28 is filled with a gas or other compressible substance.

In response to the acoustic vibrations or to generate acoustic vibrations, the electrodes 16 are electrically connected through the substrate 12 to signal processing circuitry. In one embodiment, integrated circuitry for providing a DC bias to the CMUTs, for transmit signal generation, and for received signal processing are integrated onto the substrate 12. For example, receive amplification as well as multiplexing for transmit and receive operations circuitry is integrated onto the substrate 12. Since stacked CMUTs are used, the amount of space available on the substrate for implementing circuitry is large. In one embodiment, the integrated circuitry is positioned away from the edge of the substrate 12 used for transmitting and receiving acoustic energy.

The attenuative backing material chamber 18 is filled with a material to damp acoustic energy. The attenuative backing material prevents acoustic energy from transmitting away from the desired direction. In one embodiment, the attenuative backing material chamber 18 comprises an enclosed chamber, but in other embodiments comprises a trench or open passageway.

FIG. 2 shows an array 42 of stacked CMUTs 44, 46, and 48. While the array 42 shows each stacked CMUT 44, 46, 48 as a same configuration, one or more of the stacked CMUTs 44, 46, 48 may be of a different configuration than others, such as providing interconnected chambers, a different number of layers or chambers 14, different electrical interconnections, different chamber and membrane dimensions, or other characteristics on one or more of the stacked CMUTs 46, 46, 48. By changing membrane thicknesses, shapes, volumes, diameters or other attributes, the acoustic performance of the entire array 42 or individual elements of the array are altered.

Each stacked CMUT 44, 46, 48 comprises an element of an array of azimuthally spaced elements in one embodiment. In alternative embodiments, two or more stacked CMUTs 44, 46, 48 comprise a single element within an array of transducers. FIG. 2 shows a one dimensional array 42. Additional stacked CMUTs 44, 46, 48 may be provided in an elevational dimension as part of a one dimensional array of elements or as part of a two dimensional array of elements.

In one embodiment, each stacked CMUT 44, 46, 48 comprises an individual chip or wafer of the substrate 12. Each stacked CMUT 44, 46, 48 is then arranged azimuthally and/or elevationally to provide a one dimensional or two dimensional array 42. In alternative embodiments, two or more elements or stacked CMUTs 44, 46, 48 are formed in the same chip, wafer or substrate 12.

Each stacked CMUT 44, 46, 48 is formed on the surface of the substrate. For example, the stacked CMUT 44, 46, 48 is formed in the surface of a silicon wafer. The substrate 12 or wafer is diced, etched or cut such that the stacked CMUT 44, 46, 48 radiates acoustic energy from the edge of the wafer or substrate 12. For example, a silicon wafer with a large x and y dimensions and a smaller thickness or z dimension is used. The edge along the x and z dimension radiates acoustic energy in the y dimension.

Each chamber 14 and associated membrane 24 is formed using deep reactive ion etching, wet-etch KOH-based selective etching processes or other directional processes now known or later developed for etching substrate.

After the chambers 14 are formed, the electrodes are applied with a chemical-vapor-deposition (CVD) process, such as a CVD titranium nitride processes using Parylene from Union Carbide Corp. The electrodes are applied from the edges of the chambers 14 such that the electrodes are formed on two sides of the chambers perpendicular to the direction of acoustic energy radiation. Other techniques for forming the electrodes 16 within the chambers 14 may be used.

The nongaseous filler material is deposited within the chambers 14. In one embodiment, flowable surface tension wetting effects are used to draw the nongaseous filler 40 within the chambers 14, such as depositing fluorinert materials from 3M Corp. In other embodiments, vapor deposition is used. Other processes for injecting or filling the chambers 14 with the nongaseous filler 40 may be used. The nongaseous filler material is cured in situ by UV radiation or other techniques in one embodiment.

After forming the electrode 16 and filling the chambers 14 with the nongaseous filler 40, the hole or other structure used to directionally etch the substrate 12 is filled and cured, or otherwise blocked. In alternative embodiments, the hole used for etching, depositing and filling has a labyrinth path that is not plugged or otherwise filled.

During operation, the stacked CMUTs 44, 46, 48 transduce between acoustic and electrical energies. For transmitting acoustic energy, each CMUT is driven in unison using the electrodes 16. As shown in FIG. 2, a common drive signal is applied across each chamber 14. The electrical signal causes the membranes 24 to oscillate, radiating acoustical energy in the range dimension. The power provided during transmission to each CMUT may be the same or different, such as a ratio or distribution of power that is a function of the membrane thickness or other characteristic.

Since each chamber 14 is filled with acoustically conductive low attenuation material (e.g. the nongaseious filler 40). Bottoming out or collapse of the membranes 24 is prevented. If the total height or depth of the stack of CMUTs is a fraction of the acoustic wave length, a broad band acoustic signal is generated by the stacked CMUTs 44, 46, 48. Placing the array 42 adjacent to tissue or other objects transmits the acoustic energy into the object.

For reception, acoustic energy is transmitted into the stacked CMUTs 44, 46, 48. The acoustic energy causes the membranes 24 to vibrate. In response to the vibration, electrical signals are generated on the electrode pairs within the chambers 14. The signals from each electrode pair of the stack of CMUTs contribute to an overall response. For example, the signals are integrated, added or otherwise combined. The affects of the nongaseous filler in limiting or dampening the movement of the membrane is accounted for by using the stacked CMUTs to receive the acoustic energy.

Constructing a stacked CMUT on the edge of a substrate 12 improves the efficiency such that a stacked CMUT provides a better efficiency even when filled with a nongaseous filler than the efficiency of a conventional single layer CMUT. Amplification is provided by adding more CMUTs to a stack. Since the individual membrane 24 and chambers 14 are thin, the total acoustic impedance seen through a number of such layers is close to the acoustic impedance of the typical load, such as water or a patient. The stacked CMUTs filled with nongaseous filler have an acoustic impedance of around 1.5 MRayl. Transducer efficiency is improved or not compromised since there is no need for matching layers which attenuate the acoustic energy. Improved matching provides better acoustic penetration as well as eliminating cross coupling between transducer elements through matching layers.

FIG. 3 shows a calculated acoustic impedance as a function of the number of layers where each layer comprises membranes 24 10,000 angstroms thick and water filled chambers 14 5,000 angstroms deep. The real impedance is represented by a solid line, and the imaginary impedances is represented by a dash line. Even with 16 layers, the load impedance is close to the load impedance of a single layer with the nongaseous filler below 10 megahertz. For operations within standard medical ultrasound operating frequencies, stacks of at least 10 layers of CMUTs may be used. More or fewer layers may be used based on operational preferences. With matched acoustic backing, the efficiency is improved by a factor of 5 for a 10 layer stacked CMUT as compared to a single layer CMUT. The matched acoustic backing dissipates approximately half of the power. For an air backed stack of CMUTs, an improvement factor of around 10 is provided by matched acoustic backing where the total thickness of the stacked CMUT layers is much less than the acoustic wavelength. Similar results are obtained for stacked CMUTs with 5,000 angstrom water filled chambers 14 and 20,000 angstrom membranes 24; and 2,000 angstrom water filled chambers 14 and 5,000 or 10,000 angstrom thick membranes 24.

While the invention has been described above by reference to various embodiments, it will be understood that many changes and modifications can be made without departing from the scope of the invention. For example, stacked CMUTs without a nongaseous filler may be used. A nongaseous filler may be used in a single layer CMUT device. Various performance characteristics of an array or element of a stacked CMUT may be obtained by varying dimensions and properties of the CMUTs within an element or between elements.

It is therefore intended that the foregoing detailed description be understood as an illustration of the presently preferred embodiments of the invention, and not as a definition of the invention. It is only the following claims, including all equivalents, that are intended to define the scope of the invention.

What is claimed is:

1. An ultrasonic transducer operable to transmit ultrasound radiation, the transducer comprising a substrate having plurality of chambers stacked along a dimension substantially parallel to a direction of ultrasound radiation and a plurality of membranes adjacent the respective plurality of chambers.

2. The transducer of claim 1 wherein the substrate comprises at least four chambers.

3. The transducer of claim 1 wherein the substrate comprises a wafer having an edge side, the edge side perpendicular to the direction of ultrasound radiation.

4. The transducer of claim 1 further comprising a pair of electrodes within each chamber.

5. The transducer of claim 1 wherein the substrate further comprises an acoustic signal attenuating backing material in a chamber.

6. The transducer of claim 1 further comprising a nongaseous filler within at least one of the plurality of chambers.

7. The transducer of claim 6 wherein the substrate further comprises a void connected with the plurality of chambers, the void adapted to receive expanding nongaseous filler.

8. The transduer of claim 1 wherein the substrate comprises a plurality of sets of the plurality of chambers, each set comprising an element of an array.

9. The transducer of claim 1 wherein the substrate comprises one element in an array of elements.

10. An element of an ultrasonic transducer comprising at least two capacitive microelectromechanical ultrasonic transducers (CMUTs) stacked in a range dimension.

11. The element of claim 10, wherein the element comprises at least six stacked CMUTs.

12. The element of claim 10, wherein each CMUT comprises a chamber and associated membrane.

13. The element of claim 12 further comprising a pair of electrodes within each chamber.

14. The element of claim 10, wherein at least one of the at least two CMUTs is filled with a nongaseous filler.

15. In a method for transducing between acoustic and electrical energies, an improvement comprising the act of transducing responsive to a substrate having a plurality of chambers stacked in a range dimensions wherein transducing comprises:

(a) receiving acoustic energy within each of the plurality of chambers; and (b) generating electrical signals on electrodes within the plurality of chambers in response to (a).

16. The method of claim 15 wherein transducer comprises:

(a) applying an electrical signal to electrodes within the plurality of chambers; and (b) radiating acoustic energy in the range dimension responsive to (a).

17. The method of claim 15 further comprising:

(a) damping movement of a membrane associated with one of the plurality of chambers with a nongaseous filler.

18. An ultrasonic transducer comprising:

a substrate having a chamber of a capacitive microelectromechanical ultrasonic transducer; and a nongaseous filler within the chamber.

19. The transducer of claim 18 wherein the nongaseous filler comprises a liquid.

20. The transducer of claim 18 wherein the nongaseous filler comprises a polymer.

21. The transducer of claim 18 wherein the nongaseous filler fills a portion of the chamber.

22. The transducer of claim 18 wherein the substrate further comprises a void connected with the chamber, the void adapted to receive nongaseous filler in response to pressure.

23. The transducer of claim 18 wherein the substrate comprises a plurality of chambers stacked along a dimension substantially parallel to a direction of acoustic radiation.

24. The transducer of claim 23 wherein the nongaseous filler is in each chamber and each chamber is isolated from other chambers.

25. The transducer of claim 23 wherein the nongaseous filler is in each chamber and at least two chambers interconnect.

26. The transducer of claim 18 wherein the nongaseous filler fills the entire chamber.

27. The transducer of claim 18 further comprising a pair of electrodes within the chamber.

28. The transducer of claim 18 further comprising a membrane associated with the chamber, wherein the nongaseous filler is operable to dampen movement of the membrane.

29. The transducer of claim 18 further comprising an array of elements, each element associated with at least one chamber filled with nongaseous filler.

30. A method for transducing between acoustic and electrical energies, the method comprising the acts of:

(a) transducing responsive to a substrate having a chamber; and (b) limiting collapse of the a chamber with a nongaseous filler;

wherein (a) comprises generating acoustic energy with a capacitive microelectromechanical ultrasonic transducer.

31. The method of claim 30 wherein (b) comprises limiting collapse with a liquid filler.

32. The method of claim 30 wherein (b) comprises limiting collapse with a polymer filler.

33. The method of claim 30 wherein (b) comprises damping movement of a membrane associated with the chamber with the nongaseous filler.

34. The method of claim 30 wherein (a) comprises moving a membrane in response to electrical signals from a pair of electrodes within the chamber.

35. The method of claim 30 wherein (a) comprises transducing responsive to the substrate having a plurality of chambers stacked along a dimension substantially parallel with a direction of ultrasound radiation.

* * * * *